United States Patent [19]

Müller et al.

[11] 4,041,049
[45] Aug. 9, 1977

[54] PROCESS FOR THE MANUFACTURE OF CYCLOHEXANE-1,3-DIONES AND 6-ALKYL-3,4-DIHYDRO-2-PYRANONES

[75] Inventors: Werner Heinrich Müller, Kelkheim, Taunus; Hansjörg Hey, Hofheim, Taunus; Helmut Meidert, Frankfurt am Main, all of Germany

[73] Assignee: Hoechst Aktiengesellschaft, Frankfurt am Main, Germany

[21] Appl. No.: 621,584

[22] Filed: Oct. 10, 1975

[30] Foreign Application Priority Data

Oct. 12, 1974   Germany .............................. 2448677

[51] Int. Cl.[2] ..................... C07C 45/00; C07C 45/18; C07D 309/30
[52] U.S. Cl. ............................ 260/343.5; 260/586 C; 260/590 C
[58] Field of Search ............. 260/586 C, 590 C, 343.5

[56] References Cited

U.S. PATENT DOCUMENTS

| 3,922,307 | 11/1975 | Muller | 260/586 C |
| 3,931,322 | 1/1976 | Hengartner et al. | 260/586 C |
| 3,932,511 | 1/1976 | Schaafsma et al. | 260/586 C |
| 3,950,438 | 4/1976 | Schaafsma et al. | 260/586 C |
| 3,953,514 | 4/1976 | Yamazaki et al. | 260/586 C |

OTHER PUBLICATIONS

Mannich et al., "Ber", 71:2090–2091, (1938).
Bornstein et al., "Chem. Ab.", 48:9933e (1954).
Kost et al., "Chem. Ab.", 58:13808d, (1962).

*Primary Examiner*—Norman Morgenstern
*Attorney, Agent, or Firm*—Curtis, Morris & Safford

[57] ABSTRACT

Cyclohexane-1,3-diones of the formula

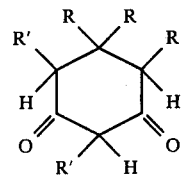

having up to 24 carbon atoms are prepared in admixture with 6-alkyl-3,4-dihydro-2-pyranones of the formula

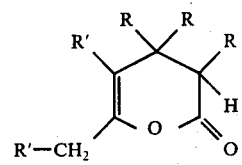

having up to 24 carbon atoms, in which formulae the radicals R and R' may be identical or different and represent each a hydrogen atom, an alkyl, a cycloalkyl or an aryl group each having up to 12 carbon atoms and the two radicals R' together optionally represent a —(CH$_2$)$_3$-group, by passing 4-oxocarboxylic acids of the formula

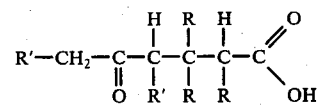

having up to 24 carbon atoms and in which R and R' have the above meaning at a temperature of from 250° to 500° C in the gaseous phase over a dehydration catalyst and the pyranones are converted into cyclohexane-1,3-diones by passing them in the gaseous phase over a dehydration catalyst at a temperature of from 250° to 500° C.

3 Claims, No Drawings

PROCESS FOR THE MANUFACTURE OF CYCLOHEXANE-1,3-DIONES AND 6-ALKYL-3,4-DIHYDRO-2-PYRANONES

The present invention relates to a catalytic gas phase process for the manufacture of cyclohexane-1,3-diones and 6-alkyl-3,4-dihydro-2-pyranones (δ-enol-lactones).

Cyclohexane-1,3-diones can be transformed by dehydrogenation into industrially important resorcinols. 6-alkyl-3,4-dihydro-2-pyranones are valuable starting materials for the manufacture of odorizing substances and can be used for the manufacture of acid derivatives of 4-oxocarboxylic acids.

It has been proposed to prepare cyclohexane-1,3,-diones in the liquid phase by reacting 6-alkyl-3,4-dihydro-pyranones or 5-oxohexanoic acid esters with sodium alcoholate. These processes have the disadvantage that at least stoichiometric amounts of sodium alcoholate must be used so that undesired sodium salts, for example sodium chloride, are necessarily formed.

To bring about cyclization of free 4-oxocarboxylic acids they are reacted with acid anhydrides or acid chlorides and anhydrous aluminum cloride in nitromethane as solvent. This type of synthesis is uneconomic since two auxiliary chemicals have to be used, both of them in a large molar excess.

δ-Enol-lactones can be synthetized from 4-oxocarboxylic acids by reacting the latter with dehydrating agents, such as, for example, acetic anhydride, acetyl chloride, or phosphorus pentachloride. In this case, too, the high amount of auxiliary required makes the synthesis uneconomic.

It is also known to prepare the δ-enol-lactone 3,4,5,6,7,8-hexahydrocoumarin in the liquid phase from the corresponding 4-oxo-carboxylic acid, namely 2(β-carboxyethyl)-cyclohexanone, by adding concentrated phosphoric or sulfuric acid. Hexahydrocoumarin and water are then removed from the reaction solution under reduced pressure.

The reason why this reaction proceeds smoothly could be attributed to the presence of the cyclohexane ring having three appropriate bonds for the formation of the six-membered ring. The same applies to the transformation of β-(1-benzyl-2-oxocyclohexyl)-propionic acid into 1-benzylbicyclo[3- 3- 1]nonane-4,9-dione with formation of a carbon-carbon bond in the presence of p-toluene-sulfonic acid in tetrahydronaphthalene. The analogous enol-lactone formation, for example of 5-oxohexanoic acid with concentrated sulfuric acid proceeds, however, very slowly with formation of considerable amounts of resin. Up to now, a process for the manufacture of cyclohexane-1,3-dione by reacting 5-oxo-hexanoic acid with p-toluene-sulfonic acid in the liquid phase has not been described.

The present invention provides a process for the manufacture of cyclohexane-1,3-diones of the formula I

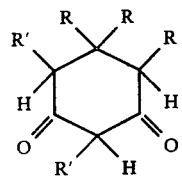

having up to 24 carbon atoms in admixture with 6-alkyl-3,4-dihydro-2-pyranones of the formula II

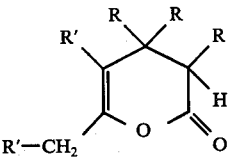

having up to 24 carbon atoms, in which formulae the radicals R and R' may be identical or different and represent each a hydrogen atom, an alkyl, a cycloalkyl, or an aryl group each having up to 12 carbon atoms and the two radicals R' together optionally represent a —(CH$_2$)$_3$ group, which comprises passing 4-oxocarboxylic acids of the formula III

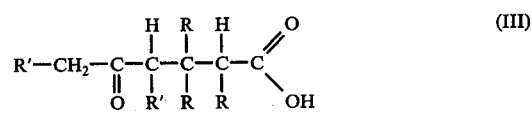

having up to 24 carbon atoms in which R and R' have the above meaning at a temperature of from 250° to 500° C in the gaseous phase over a dehydration catalyst.

The present invention also provides a process for the manufacture of cyclohexane-1,3-diones having up to 24 carbon atoms and the formula I as defined above, which comprises passing 6-alkyl-3,4-dihydro-2-pyranones having up to 24 carbon atoms of formula II as defined above at a temperature in the range of from 250° to 500° C over a dehydration catalyst.

4-Oxo-carboxylic acids are in an equilibrium with the corresponding enol-lactone and water as follows:

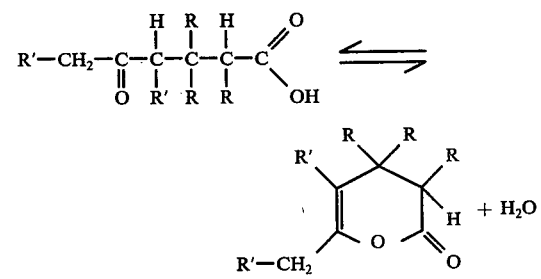

At the relatively high temperatures of the process of the invention the proportion of enol-lactones in the above equilibrium is high while the carboxylic acid is formed again on cooling. The speed at which the equilibrium is adjusted depends on the temperature. At room temperature, for example, 6-methyl-3,4-dihydro-2-pyranone and water react for several hours, whereas at a temperature of 100° to 150° C the reaction to 5-oxohexanoic acid is substantially terminated after a few minutes. The catalysts to be used according to the invention accelerate the formation of the equilibrium.

When the δ-enol-lactone is to be isolated from the mixture of cyclohexane-dione, δ-enol-lactone, water and unreacted 4-oxocarboxylic acid care must be taken that the lactone does not react with the reaction water to form 4-oxocarboxylic acid. Therefore, the reaction water must be immediately removed from the equilibrium, for example by vacuum distillation or distillation using an entrainer. In this manner a selectivity of δ-enol-lactone of up to 80% can be obtained.

If, however, an isolation of the δ-enol-lactone is not desired it is not prevented from hydrolyzing to 4- oxocarboxylic acid. In this case a selectivity of cyclohexane-dione of over 90% can be reached.

Suitable starting compounds for the manufacture of cyclohexanediones are 4-oxocarboxylic acids as well as δ-enol-lactones or mixtures of the acids and the lactones.

In the starting compounds the substituents R and R' may be identical or different and each represent a hydrogen atom, an alkyl, a cycloalkyl, or an aryl group each having up to 12 carbon atoms, alkyl or cycloalkyl groups having up to 6 carbon atoms being preferred and preferred aromatic groups are the phenyl and naphthyl group.

Especially suitable starting compounds are 5-oxohexanoic acid, 5-oxoheptanoic acid, 4-methyl-5-oxo-hexanoic acid, 4-methyl-5-oxoheptanoic acid, 4-propyl-5-oxohexanoic acid, 4-hexyl-5-oxo-hexanoic acid, 4-phenyl-5-oxohexanoic acid, 2-methyl-5-oxohexanoic acid and 3-methyl-5-oxohexanoic acid, 3-(2-oxocyclohexyl)-propionic acid, and the corresponding δ-enol-lactones.

The 4-oxocarboxylic acids can be readily prepared in the presence of primary amines as catalyst by reacting ketones having one or several active hydrogen atoms in α-position with α,β-unsaturated carboxylic acids, or by saponification of the esters or nitriles of the 4-oxocarboxylic acids which are also readily accessible.

It is surprising that the 4-oxocarboxylic acids can be transformed in a high space-time-yield in the gaseous phase into the two cyclization products without losses in yield occuring in spite of the high reaction temperatures by carbonization or oligomerization reactions, which would rapidly reduce the catalyst activity.

Suitable dehydration catalysts in the process of the invention are weakly basic or acid oxides, for examples oxides of magnesium, zinc, cadmium; oxides of the elements of the third and fourth subgroups of the period table, the oxides of tungsten, iron, or aluminum, as well as silicon dioxide. The oxides can be used alone or in admixture with one another or in the form of mixed oxides. Acidic γ-aluminum oxide, aluminum silicates, titanium dioxide in the anatase modification, thorium oxide, and tungsten pentoxide having very good catalytic properties.

The catalytically active oxides can be used directly, for example in the form of tablets or in extruded form or they may be applied in known manner to an inert carrier material, for example by impregnating the carrier material with an aquous solution of an inorganic salt. By heating the impregnated carrier material the metal oxide forms directly on the carrier, optionally after a pretreatment, for example with ammonia.

Further suitable dehydration catalysts are phosphoric acid, polyphosphoric acid and the salts thereof, for example aluminum phosphate on a carrier material.

Especially preferred are commercial catalysts on carrier material having an acidic surface and consisting of γ-aluminum oxide or aluminum silicates.

The catalysts can be used in a fixed bed or a fluidized bed.

To carry out the process of the invention the starting compound is passed, either alone or in admixture with an inert additive, for example nitrogen or benzene, in the gaseous state over the catalyst heated to 250° to 500° C, preferably 280° to 420° C. The reaction products are subsequently condensed and worked up.

The pressure under which the process of the invention is carried out is not critical. In general, the reaction is carried out under a pressure in the range of from 10 millibar to 10 bar. The gases to be reacted remain in contact with the catalyst layer preferably from 0.1 to 5 seconds, although longer or shorter contact times are also possible. The starting compounds can be vaporized per se or together with acetic acid, benzene, hexane, water, or another solvent or solvent mixture and passed over the catalyst, optionally together with an inert gas, for example nitrogen, hydrogen, carbon dioxide, or methane.

The following examples illustrate the invention. To carry out the reaction the starting products were passed, together with the diluent, first into an evaporator and then through a glass reactor having a length of 70 cm and a diameter of 2 cm. The glass tube was heated by an electric furnace. In the center part it contained a 17 cm layer (75 ml) of catalyst. The temperature in the layer was measured with a thermocouple which could be displaced in a small glass tube concentrically mounted in the reactor. The catalyst granules had a diameter of 1 to 2 mm. After having left the reactor, the reaction gases were condensed in two traps cooled to −80° C.

At intervals of 30 to 60 minutes samples were taken and analyzed by gas chromatography. For evaluation only those samples were considered the concentrations of which had reached constant values 2 to 4 hours after the start of the reaction.

The products were identified by comparison with products synthesized in different manner by combination of gas chromatography, mass spectroscopy and NMR spectra.

EXAMPLE 1

30 g (0.23 mol) 5-oxohexanoic acid and 1.6 mols $N_2$ were passed per hour over a commercial catalyst 1 heated to 330 ± 5° C and consisting of 13% $Al_2O_3$ and 87% $SiO_2$, having a pore volume of 0.34 ml $H_2O$ per gram, a "mean pore diameter" of 143 A and a surface area of 95 m$^2$/g. The reaction product (30 g) contained 12.8% by weight cyclohexane-1,3-dione. 42% by weight 6-methyl-3,4-dihydro-2-pyranone, 9% by weight $H_2O$ and 36.4 % by weight unreacted 5-oxohexanoic acid. With a conversion of 63.5 mol % of 5-oxohexanoic acid the selectivity of cyclohexane-1,3-dione was 23.4 mol % and of δ-enol-lactone it was 76.6 mol %, the respective yields being 14.9 and 48.8 mol %. After about 24 hours at room temperature approximately 90% of the δ-enol-lactone had reacted with the water to form again 5-oxohexanoic acid. Referred to the 5-oxo-hexanoic acid equivalents, i.e. the sum of acid and lactone, the selectivity of cyclohexane-1,3-dione was practically 100 mol %.

COMPARATIVE EXAMPLE 1

The reaction was carried out as specified in Example 1, with the exception that the reactor was charged with glass beads instead of the catalyst. In the condensate neither cyclohexane-1,3-dione nor δ-enol-lactone could be detected. The 5-oxohexanoic acid was quantitatively recovered.

COMPARATIVE EXAMPLE 2

The reaction was carried out as specified in Example 1 with the exception that α-aluminum oxide having a pore volume of 0.2 ml $H_2O$/g, 82.5% of the total pore volume being formed by pores having a diameter greater than 75,000 A, and a surface area of 0.1 m$^2$/g was used as catalyst. At a temperature of 400° ± 10° C a reaction product was obtained which contained 3% by weight cyclohexane-1,3-dione and 3% by weight 6-methyl-3,4-dihydro-2-pyranone. At a reaction temperature of 340° ± 10° C the two cyclization products could be hardly detected.

EXAMPLE 2

The reaction was carried out under the conditions specified in Example 1 but with a commercial catalyst 2 consisting of 45% by weight $Al_2O_3$ and 55% by weight $SiO_2$ and having a pore volume of 0.74 ml $H_2O/g$ and a surface area of 420 m²/g. At a reaction temperature of 360° ± 5° C 32 mol % cyclohexane-1,3-dione were obtained.

EXAMPLES 3 to 8

The reactions were carried out under the conditions specified in the following Table 1 with the following catalysts: Catalyst 1 as defined in Example 1;

Catalyst 3 commercial γ-aluminum oxide (99.8% $Al_2O_3$, pore volume 0.6 ml $H_2O/g$, mean pore diameter 400 A, i.e. 50% of the total pore volume was formed by pores having a diameter d of less than 400 A and 50% was formed by pores having a diameter d greater than 400 A, the surface area being 60 m²/g;

Catalyst 4 commercial γ-aluminum oxide (99.8% $Al_2O_3$ having a pore volume of 0.60 ml $H_2O/g$, a mean pore diameter of 300 A and a surface area of 80 m²/g;

Catalyst 5 α-aluminum oxide as used in Comparative Example 2 impregnated with 15% by weight phosphoric acid.

The results are indicated in Table 1.

EXAMPLES 9 to 11

22.5 g 4-oxocarboxylic acid of the formula $$R^1CH_2COCHR^2(CH_2)_2COOH$$

(for the meaning of $R^1$ and $R^2$ cf. Table 2) were passed per hour together with 1.4 mol $H_2$ at a temperature of 300° ± 5° C over a catalyst 6 (commercial γ-aluminum oxide consisting of 99.8% $Al_2O_3$ and having a pore volume of 0.57 ml $H_2O/g$, a "mean pore diameter" of 120 A and a surface area of 100 m²/g. The results are indicated in Table 2.

TABLE 1

| Example No. | starting product (mmols/h) | diluent (mol/h) | | catalyst | temperature ° C | conversion (mol %) of 5-oxohexanoic acid equivalents *) | selectivity (mol %) of cyclohexane-1,3-dione, calc. on 5-oxohexanoic acid equivalents *) |
|---|---|---|---|---|---|---|---|
| 3 | 5-oxohexanoic acid (230) | $N_2$ | (1.6) | 3 | 340±8 | 18 | 95 |
| 4 | 5-oxohexanoic acid (230) | $N_2$ | (1.6) | 4 | 340±10 | 35 | 70 |
| 5 | 5-oxohexanoic acid (230) | $N_2$ | (1.6) | 1 | 360±8 | 26 | 80 |
| 6 | 5-oxohexanoic acid (41.5) | $H_2O$ (1.2); $N_2$ | (1.24) | 1 | 335±15 | 24.5 | 90 |
| 7 | 6-methyl-3,4-dihydro-2-pyranone (535) | $N_2$ | (1.6) | 1 | 415±5 | 8 | 85 |
| 8 **) | 5-oxohexanoic acid (230) | $N_2$ | (1.6) | 5 | 330±5 | 7.3 | 45 |

*) 1 mol 5-oxohexanoic acid equivalents means x mols 5-oxohexanoic acid and 1 − x mols δ-enol-lactone, x≦1.
**) the reaction product of Example 8 contained 65 % by weight 5-oxohexanoic acid and 24 % by weight 6-methyl-3,4-dihydro-2-pyranone, consequently the enol-lactone is obtained with a selectivity of 80 mol %.

TABLE 2

| Example No. | acid used $R^1CH_2COCHR^2(CH_2)_2COOH$ with | | conversion of acid (mol %) | selectivities (mol %) | |
|---|---|---|---|---|---|
| | $R^1$ | $R^2$ | | δ-enol lactone *) | cyclohexane 1,3-dione derivative **) |
| 9 | H | $CH_3$ | 53 | 40 | 83 |
| 10 | $CH_3$ | H | 63 | 15 | 62 |
| 11 | $CH_3$ | $CH_3$ | 55 | 17 | 82 |

*) calculated on converted acid
**) calculated on converted δ-ketocarboxylic acid equivalents

What is claimed is:
1. A process for the manufacture of cyclohexane-1,3-diones of the formula I

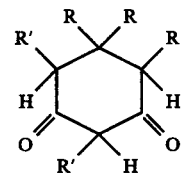

(I)

having up to 24 carbon atoms in admixture with 6-alkyl-3,4-dihydro-2-pyranones of the formula II

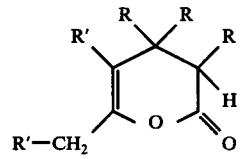

(II)

having up to 24 carbon atoms, in which formulae the radicals R and R' may be identical or different and each represent a hydrogen atom, an alkyl, a cycloalkyl or an aryl group each having up to 12 carbon atoms and the two radicals R' together optionally represent a —(CH₂)₃-group, which comprises passing 4-oxocarboxylic acids of the formula III

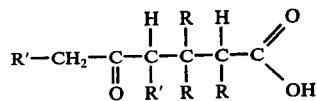
(III)

having up to 24 carbon atoms and in which R and R' have the above meaning at a temperature of from 250° to 500° C in the gaseous phase over a dehydration catalyst.

2. The process of claim 1, wherein the catalyst is phosphoric acid or polyphosphoric acid supported on an inert carrier material.

3. The process of claim 1, wherein the catalyst is γ-aluminum oxide, titanium dioxide in the anatase modification, thorium oxide, tungsten oxide, silicon dioxide, zirconium dioxide, a mixture thereof or a mixed oxide thereof, or an aluminum silicate.